US00PP25352P2

(12) United States Plant Patent
Kanazawa

(10) Patent No.: US PP25,352 P2
(45) Date of Patent: Mar. 17, 2015

(54) *ANEMONE* PLANT NAMED 'POCAHONTAS'

(50) Latin Name: *Anemone hupehensis*
Varietal Denomination: Pocahontas

(71) Applicant: Yoshihiro Kanazawa, Yamaturi-Machi (JP)

(72) Inventor: Yoshihiro Kanazawa, Yamaturi-Machi (JP)

(73) Assignee: Osco Garden B.V., Aalsmeer (NL)

( * ) Notice: Subject to any disclaimer, the term of this patent is extended or adjusted under 35 U.S.C. 154(b) by 125 days.

(21) Appl. No.: 13/815,652

(22) Filed: Mar. 13, 2013

(51) Int. Cl.
*A01H 5/00* (2006.01)

(52) U.S. Cl.
USPC ..... Plt./263.1

(58) Field of Classification Search
CPC ..... A01H 5/02; A01H 5/00; A01H 5/025; A01H 5/12
USPC ..... Plt./263.1
See application file for complete search history.

*Primary Examiner* — June Hwu
(74) *Attorney, Agent, or Firm* — C. A. Whealy

(57) ABSTRACT

A new and distinct cultivar of *Anemone* plant named 'Pocahontas', characterized by its upright and compact plant habit; moderately vigorous growth habit; freely flowering habit; semi-double-type flowers that are light purple in color; and good garden performance.

2 Drawing Sheets

Botanical designation: *Anemone hupehensis.*
Cultivar denomination: 'POCAHONTAS'.

BACKGROUND OF THE INVENTION

The present invention relates to a new and distinct cultivar of *Anemone*, botanically known as *Anemone hupehensis* and hereinafter referred to by the name 'Pocahontas'.

The new *Anemone* plant is a product of a planned breeding program conducted by the Inventor in Yamatsuri-machi, Fukushima-ken, Japan. The objective of the breeding program is to create new compact *Anemone* plants with numerous attractive flowers.

The new *Anemone* plant originated from a cross-pollination made by the Inventor in October, 1995 in Yamatsuri-machi, Fukushima-ken, Japan of an unnamed proprietary selection of *Anemone hupehensis*, not patented, as the female, or seed, parent, with *Anemone hupehensis* 'Diana', not patented, as the male, or pollen, parent. The new *Anemone* plant was discovered and selected by the Inventor as a single flowering plant within the progeny of the stated cross-pollination in a controlled greenhouse environment in Yamatsuri-machi, Fukushima-ken, Japan in October, 1997.

Asexual reproduction of the new *Anemone* by root cuttings in a controlled environment in Yamatsuri-machi, Fukushima-ken, Japan since October, 1997 has shown that the unique features of this new *Anemone* plant are stable and reproduced true to type in successive generations.

SUMMARY OF THE INVENTION

Plants of the new *Anemone* have not been observed under all possible environmental conditions and various cultural practices. The phenotype may vary somewhat with variations in environmental conditions such as temperature and light intensity without, however, any variance in genotype.

The following traits have been repeatedly observed and are determined to be the unique characteristics of 'Pocahontas'.

These characteristics in combination distinguish 'Pocahontas' as a new and distinct *Anemone* plant:

1. Upright and compact plant habit.
2. Moderately vigorous growth habit.
3. Freely flowering habit.
4. Semi-double-type flowers that are light purple in color.
5. Good garden performance.

Plants of the new *Anemone* can be compared to plants of the female parent selection. Plants of the new *Anemone* differ primarily from plants of the female parent selection in the following characteristics:

1. Plants of the new *Anemone* have stronger roots than plants of the female parent selection.
2. Plants of the new *Anemone* are more freely flowering than plants of the female parent selection have single type flowers.
3. Plants of the new *Anemone* have semi-double-type flowers whereas plants of the female parent selection have single-type flowers.

Plants of the new *Anemone* can be compared to plants of the male parent, 'Diana'. Plants of the new *Anemone* differ primarily from plants of 'Diana' in the following characteristics:

1. Plants of the new *Anemone* are more compact than plants of 'Diana'.
2. Plants of the new *Anemone* have stronger roots than plants of 'Diana'.
3. Plants of the new *Anemone* and 'Diana' differ in flower color as plants of 'Diana' have pink-colored flowers.

Plants of the new *Anemone* can be compared to plants of *Anemone hupehensis* 'Pretty Lady Susan', disclosed in U.S. Plant Pat. No. 22,331. In side-by-side comparisons conducted in Mijdrecht, The Netherlands, plants of the new *Anemone* and 'Pretty Lady Susan' differed primarily in the following characteristics:

1. Plants of the new *Anemone* were more compact than plants of 'Pretty Lady Susan'.

2. Plants of the new *Anemone* flowered later than plants of 'Pretty Lady Susan'.
3. Plants of the new *Anemone* had semi-double-type flowers whereas plants of 'Pretty Lady Susan' had single-type flowers.
4. Plants of the new *Anemone* and 'Pretty Lady Susan' differed in flower color as plants of 'Pretty Lady Susan' had deep pink-colored flowers.

BRIEF DESCRIPTION OF THE PHOTOGRAPHS

The accompanying colored photographs illustrate the overall appearance of the new *Anemone* plant showing the colors as true as it is reasonably possible to obtain in colored reproductions of this type. Colors in the photographs may differ slightly from the color values cited in the detailed botanical description which accurately describe the colors of the new *Anemone* plant.

The photograph on the first sheet is a side perspective view of a typical plant of 'Pocahontas' in a container.

The photograph on the second sheet comprises a close-up view of a typical flower of 'Pocahontas'.

DETAILED BOTANICAL DESCRIPTION

The aforementioned photographs and following observations, measurements and values describe plants grown in 17-cm containers during the summer in an outdoor nursery in Mijdrecht, The Netherlands and under cultural practices typical of commercial *Anemone* production. During the production of the plants, day temperatures ranged from 14° C. to 28° C. and night temperatures ranged from 6° C. to 16° C. Plants were four months old when the photographs and description were taken. In the following description, color references are made to The Royal Horticultural Society Colour Chart, 2007 Edition, except where general terms of ordinary dictionary significance are used.

Botanical classification: *Anemone hupehensis* 'Pocahontas'.

Parentage:

*Female, or seed, parent*.—Unnamed proprietary selection of *Anemone hupehensis*, not patented.

*Male, or pollen, parent*.—*Anemone hupehensis* 'Diana', not patented.

Propagation:

*Type*.—In vitro propagation.

*Time to initiate roots, summer*.—About 15 days at temperatures of 20° C. to 25° C.

*Time to initiate roots, winter*.—About 25 days at temperatures of 15° C. to 20° C.

*Root description*.—Medium in thickness, fleshy; white in color.

*Rooting habit*.—Moderately freely branching; medium density.

Plant description:

*Plant and growth habit*.—Herbaceous perennial; upright and compact plant habit with leaves developing from basal rosettes; about six basal rosettes developing per plant; moderately vigorous growth habit.

*Plant height*.—About 41.8 cm.

*Plant diameter*.—About 32.1 cm.

Foliage description:

*Arrangement*.—Alternate, compound with three leaflets per leaf.

*Length, leaves*.—About 9.2 cm.

*Width, leaves*.—About 8.8 cm.

*Length, leaflets*.—About 6 cm.

*Width, leaflets*.—About 3.1 cm.

*Shape, leaves*.—Broadly ovate.

*Shape, leaflets*.—Ovate to broadly ovate.

*Apex, leaflets*.—Acute.

*Base, leaflets*.—Obtuse to hastate.

*Margin, leaflets*.—Serrate.

*Texture, leaflets, upper and lower surfaces*.—Pubescent.

*Venation pattern, leaflets*.—Palmate, laciniate.

*Color*.—Developing leaflets, upper surface: Close to 143A. Developing leaflets, lower surface: Close to 138B. Fully expanded leaflets, upper surface: Close to N137A; venation, close to 144A. Fully expanded leaflets, lower surface: Close to 147B; venation, close to 144A.

*Leaf petiole*.—Length: About 9.8 cm. Diameter: About 2 mm. Texture, upper and lower surfaces: Smooth, glabrous. Color, upper and lower surfaces: Close to 144A.

Flower description:

*Flower arrangement and flowering habit*.—Semi-double-type rose-like flowers arranged in simple and compound cymes; freely flowering habit with eight flowers develop per inflorescence and about 48 flowers developing per plant; flowers face mostly upright to slightly outwardly.

*Fragrance*.—None detected.

*Natural flowering season*.—Plants of the new *Anemone* begin flowering about 10.5 months after planting and flower during the late summer in The Netherlands.

*Flower longevity*.—Individual flowers last about one week on the plant; flowers not persistent.

*Inflorescence height*.—About 14.3 cm.

*Inflorescence diameter*.—About 16.5 cm.

*Flower diameter*.—About 5.3 cm.

*Flower length (depth)*.—About 1.8 cm.

*Flower buds*.—Length: About 9 mm. Diameter: About 1 cm. Shape: Globular. Color: Close to 178A; stripes, close to N187C to N187D; base tinged with close to 145A to 145B.

*Petals*.—Absent.

*Sepals*.—Quantity and arrangement: About 19 arranged in two to three whorls. Length: About 2.5 cm to 2.6 cm. Width: About 1.2 cm to 1.6 cm. Shape: Obovate to elliptic. Apex: Obtuse or emarginate. Base: Acute. Margin: Entire. Texture, upper surface: Glabrous, smooth, velvety. Texture, lower surface: Densely pubescent. Color: When opening, upper surface: Close to between 76C and N77B; towards the base, close to 144D. When opening, lower surface: Close to between 77C to 77D and N77B; towards the base, close to 144D. Fully opened, upper surface: Close to between 77B to 77C and N77B; towards the base, close to 144D; color does not fade with development. Fully opened, lower surface: Close to between 77C to N77B; towards the base, close to 144D.

*Peduncles*.—Length: About 18.8 cm. Diameter: About 3 mm. Aspect: Mostly erect to 37.5° from vertical. Strength: Moderately strong. Color: Close to 144A.

*Pedicels*.—Length: About 6.5 cm. Diameter: About 1 mm. Aspect: Erect to about 40° from the peduncle axis. Strength: Strong. Color: Close to 138B to 138C tinged with close to 201B to 201C.

*Reproductive organs*.—Androecium: Stamen number per flower: About 170. Filament length: About 5 mm. Filament color: Close to NN155C to NN155D.

Anther shape: Reniform. Anther length: About 1 mm. Anther color: Close to 14A. Amount of pollen: Scarce. Pollen color: Close to 12A. Gynoecium: Pistil number per flower: About 200. Pistil length: About 1 mm. Stigma shape: Club-shaped. Stigma color: Close to 144B. Style length: About 0.5 mm. Style color: Close to 145A. Ovary color: Close to 145A.

*Seeds and fruits*.—Seed and fruit development have not been observed on plants of the new *Anemone*.

Garden performance: Plants of the new *Anemone* have been observed to have good garden performance, to tolerate high temperatures of about 35° C. and to be hardy to USDA Hardiness Zone 4.

Pathogen & pest resistance: Plants of the new *Anemone* have not been observed to be resistant to pests and pathogens common to *Anemone* plants.

It is claimed:

1. A new and distinct *Anemone* plant named 'Pocahontas' as illustrated and described.

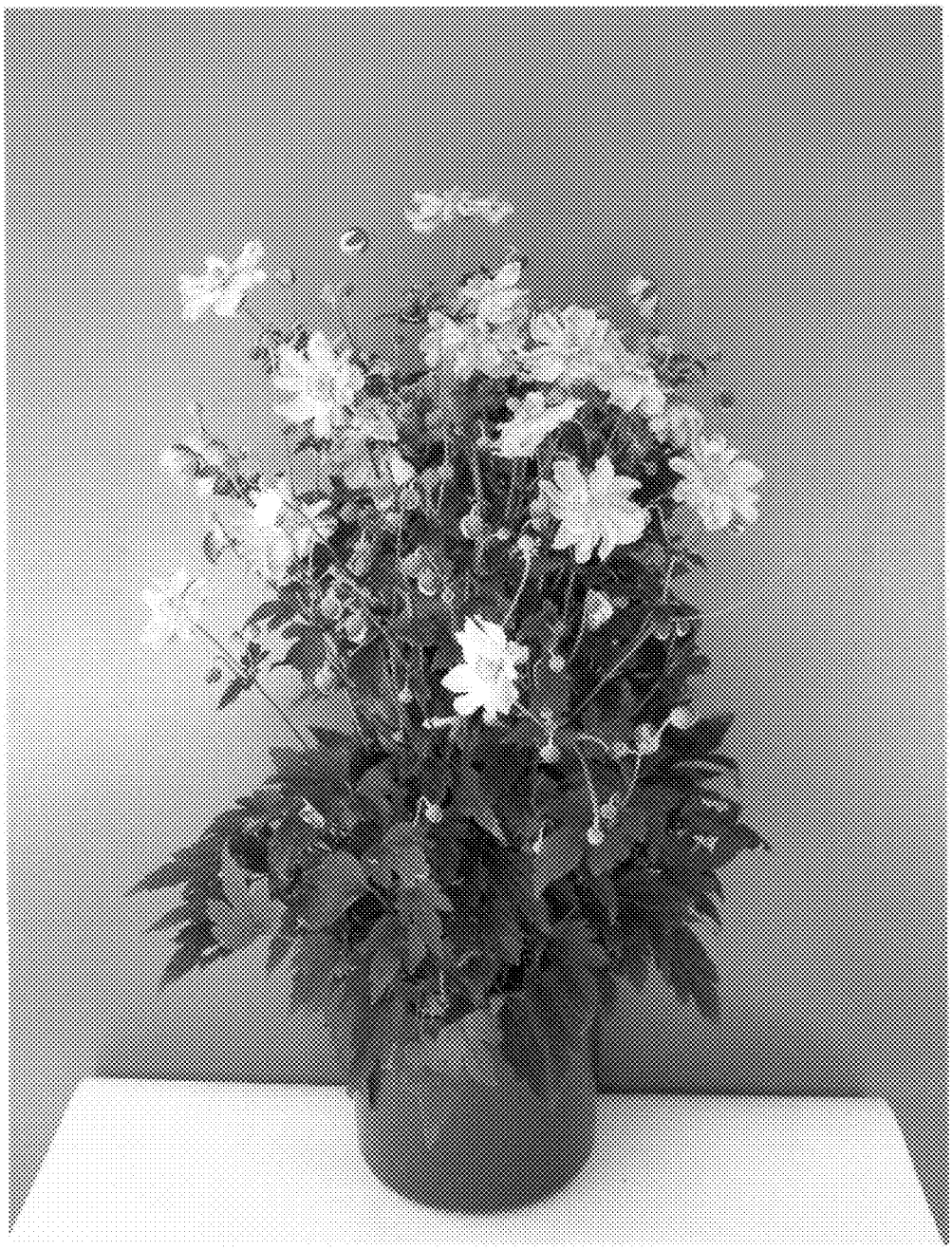

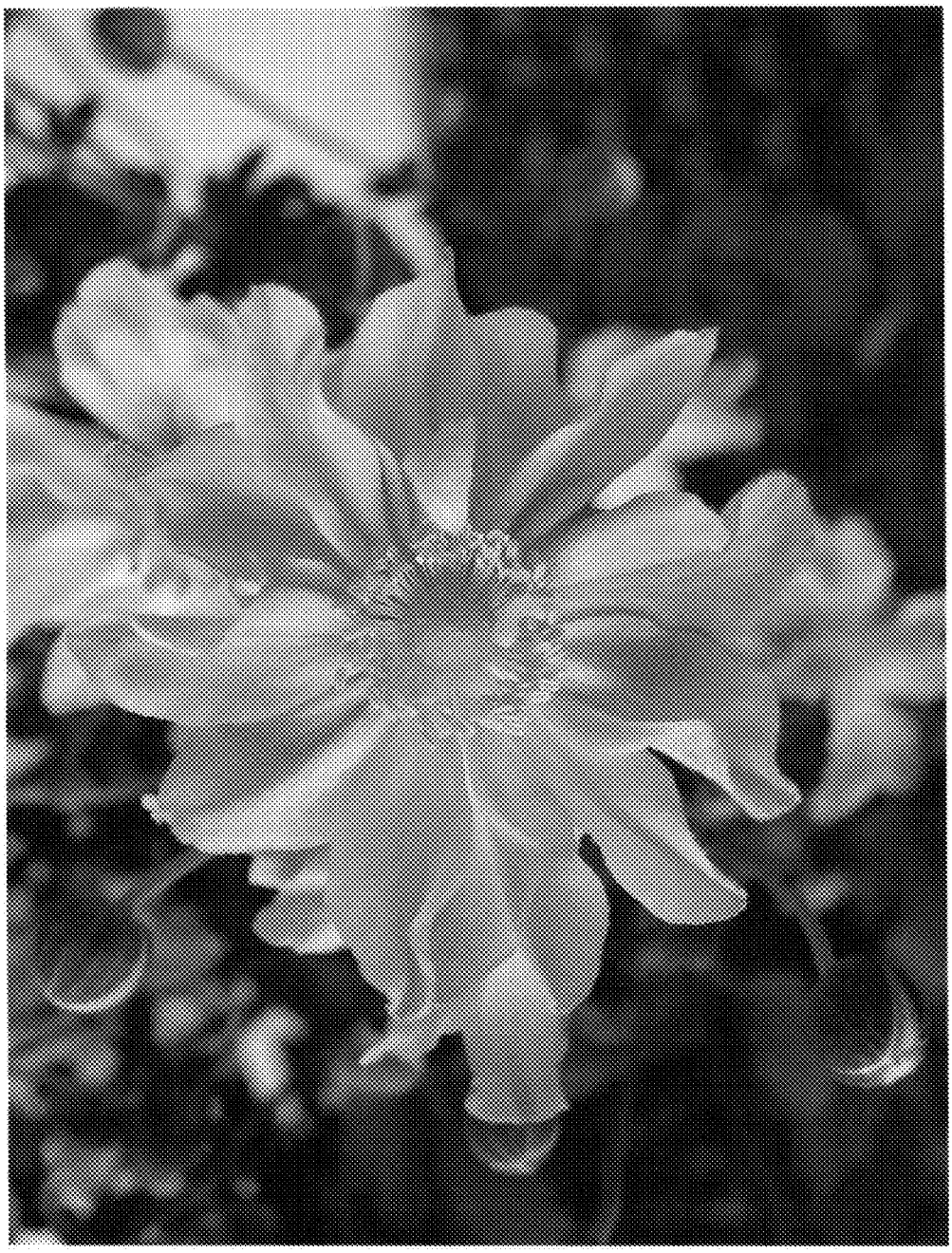

* * * * *